United States Patent
Wang

(10) Patent No.: US 9,706,940 B2
(45) Date of Patent: Jul. 18, 2017

(54) CLOCK

(71) Applicant: Wei-Yao Wang, Taipei (TW)

(72) Inventor: Wei-Yao Wang, Taipei (TW)

( * ) Notice: Subject to any disclaimer, the term of this patent is extended or adjusted under 35 U.S.C. 154(b) by 77 days.

(21) Appl. No.: 14/823,190

(22) Filed: Aug. 11, 2015

(65) Prior Publication Data

US 2016/0266550 A1 Sep. 15, 2016

(30) Foreign Application Priority Data

Mar. 11, 2015 (CN) .......................... 2015 1 0105307

(51) Int. Cl.
| | |
|---|---|
| *G04G 9/00* | (2006.01) |
| *A61B 5/0482* | (2006.01) |
| *F41J 3/00* | (2006.01) |
| *A63F 9/24* | (2006.01) |
| *A63F 13/00* | (2014.01) |
| *A63F 13/212* | (2014.01) |
| *A61B 5/00* | (2006.01) |
| *A61B 5/04* | (2006.01) |

(52) U.S. Cl.
CPC ............ *A61B 5/0482* (2013.01); *A61B 5/742* (2013.01); *A61B 5/7475* (2013.01); *A63F 9/24* (2013.01); *A63F 13/00* (2013.01); *A63F 13/212* (2014.09); *F41J 3/0009* (2013.01); *G04G 9/0064* (2013.01); *A61B 5/04012* (2013.01)

(58) Field of Classification Search
CPC ............ G04G 9/0064; G04G 9/02; A63F 9/24
USPC .................................... 368/83, 239, 240, 241
See application file for complete search history.

(56) References Cited

U.S. PATENT DOCUMENTS

| | | | | |
|---|---|---|---|---|
| 4,041,692 A | * | 8/1977 | Marshino ............... | G04G 9/042 368/240 |
| 4,920,524 A | * | 4/1990 | Kotob ...................... | G04G 9/04 368/240 |
| 5,253,228 A | * | 10/1993 | Truett ..................... | G04F 1/005 368/107 |
| 5,829,755 A | * | 11/1998 | Chen ......................... | F41J 3/02 273/371 |
| 7,385,879 B2 | * | 6/2008 | Kibiloski ............... | G04C 10/04 368/203 |
| 2003/0109797 A1 | * | 6/2003 | Kim ...................... | A61B 5/0482 600/545 |
| 2004/0013042 A1 | * | 1/2004 | Farine .................. | G04G 17/005 368/10 |
| 2009/0028005 A1 | * | 1/2009 | You ........................ | G04G 21/00 368/10 |
| 2009/0218769 A1 | * | 9/2009 | Krzewicki ............. | A63D 15/20 273/374 |
| 2012/0299244 A1 | * | 11/2012 | Rice ...................... | F41J 3/0028 273/407 |
| 2013/0167074 A1 | * | 6/2013 | Oonishi ................ | G06F 3/0488 715/799 |

(Continued)

*Primary Examiner* — Amy Cohen Johnson
*Assistant Examiner* — Jason Collins
(74) *Attorney, Agent, or Firm* — Muncy, Geissler, Olds & Lowe, P.C.

(57) ABSTRACT

A clock is adapted to operate in a first mode and a secondary mode. The clock includes a body having a display surface. When the clock operates in the first mode, the clock displays a time information on the display surface. When the clock operates in the secondary mode, the clock acts as a dart and receives at least one external signal. The clock displays at least one interactive information on the display surface according to the external signal.

15 Claims, 15 Drawing Sheets

(56) References Cited

U.S. PATENT DOCUMENTS

2013/0210507 A1\* 8/2013 Wayans ................. A63F 13/06
 463/7
2014/0071069 A1\* 3/2014 Anderson ............... A63F 13/06
 345/173

\* cited by examiner

CLOCK

CROSS REFERENCE TO RELATED APPLICATIONS

This Non-provisional application claims priority under 35 U.S.C. §119(a) on Patent Application No(s). 201510105307.2 filed in China on Mar. 11, 2015, the entire contents of which are hereby incorporated by reference.

BACKGROUND

Technical Field

The invention relates to a dual mode clock.

Related Art

Brainwave is a kind of signal of electric current activity in brain. General brainwave is classified into α wave, β wave, θ wave or δ wave, etc. according to frequency. When the α-wave occupies higher proportion of ingredients, it means that the man is conscious and concentrative, and this is the best state for the man to learn or think; when the β-wave occupies higher proportion of ingredients, it means that the man is nervous and uneasy, and the man will easily feel enormous pressure and it causes immunity to fall down if he is at this state over a long period of time; when the θ-wave occupies higher proportion of ingredients, it means that the man is extremely relaxed, and the deep memory of the man can be triggered; when the δ-wave occupies higher proportion of ingredients, it means that the man is unconscious at sleep state. No δ-wave is issued from an ordinary man when he is conscious.

Because the brainwave can indicate various physiological and psychological state of the human body, the brainwave detection device can be utilized to detect the brainwave of the human body to obtain the result corresponding to instant health and psychological state of the human body, for example applying to determination of the testee's concentration, as a follow-up concentration-related application.

Although currently there are various technologies to detect brainwave information, their applications especially those of concentration-related brainwave information are still in development.

Therefore, it is important to provide an interactive system and its display device and brainwave detection device which can issue a concentration-related signal according to the detected brainwave information to perform related application.

SUMMARY

The invention provides an interactive system and its display device and brainwave detection device which can issue a concentration-related signal according to the detected brainwave information to perform related application An interactive system according to the invention includes a brainwave detection device and a display device. The brainwave detection device detects the brainwave information of a user, and issues a concentration-related signal according to the brainwave information. The display device has a first display zone. The first display zone displays a plurality of patterns. The display device receives the concentration-related signal, and decides the display duration of at least one of the patterns according to the concentration-related signal.

In one embodiment, the interactive system cooperates with an electronic device. The display device receives the concentration-related signal through the electronic device.

In one embodiment, the interactive system cooperates with an electronic device. When the electronic device issues an executing signal, the display device receives the executing signal and takes the correspondingly displayed pattern upon receiving the executing signal as a first interactive result.

In one embodiment, the display device further includes a secondary display zone. The secondary display zone has a plurality of sensors. The display device decides the number of the sensors to enable according to the concentration-related signal.

In one embodiment, the display device further includes a secondary display zone. The secondary display zone has a plurality of light units. The display device decides the number of the light units taken to light according to the concentration-related signal, and the higher the concentration of the user is, the more the number of the light units taken to light is.

In one embodiment, when an electronic device issues an executing signal, the display device receives the executing signal and takes the state of the light units correspondingly taken to light upon receiving the executing signal as a secondary interactive result.

In one embodiment, the patterns surround the secondary display zone, and the patterns are displayed clockwise, counterclockwise or randomly in turn.

In one embodiment, the user executes a default operation by the electronic device to issue the executing signal.

In one embodiment, the default operation is swaying the electronic device or touching a default zone on the electronic device.

In one embodiment, the pattern includes a numeral or a design.

A display device according to the invention cooperates with a brainwave detection device. The brainwave detection device detects the brainwave information of a user and issues a concentration-related signal according to the brainwave information. The display device includes a first display zone. The first display zone displays a plurality of patterns. The display device receives the concentration-related signal and decides the display duration of at least one of the patterns according to the concentration-related signal.

In one embodiment, the display device cooperates with an electronic device. The display device receives the concentration-related signal through the electronic device.

In one embodiment, the display device cooperates with an electronic device. When the electronic device issues an executing signal, the display device receives the executing signal and takes the corresponding pattern upon receiving the executing signal as a first interactive result.

In one embodiment, the display device further includes a secondary display zone. The secondary display zone has a plurality of sensors. The display device decides the number of the sensors to enable according to the concentration-related signal.

In one embodiment, the display device further includes a secondary display zone. The secondary display zone has a plurality of light units. The display device decides the number of the light units taken to light according to the concentration-related signal. The higher the concentration of the user is, the more the number of the light units taken to light is.

In one embodiment, when an electronic device issues an executing signal, the display device receives the executing signal and takes the state of the light units correspondingly taken to light upon receiving the executing signal as a secondary interactive result.

In one embodiment, the patterns surround the secondary display zone, and the patterns are displayed clockwise, counterclockwise or randomly in turn.

In one embodiment, the user executes a default operation by the electronic device to issue the executing signal.

In one embodiment, the default operation is swaying the electronic device or touching a default zone on the electronic device.

In one embodiment, the pattern includes a numeral or a design.

A brainwave detection device according to the invention cooperates with an electronic device and a display device. The display device has a first display zone. The first display zone displays a plurality of patterns. The brainwave detection device includes a detection electrode. The detection electrode detects the brainwave information of a user, and issues a concentration-related signal according to the brainwave information. The display device receives the concentration-related signal and decides the display duration of at least one of the patterns according to the concentration-related signal.

In one embodiment, the display device receives the concentration-related signal through the electronic device.

In one embodiment, the display device further includes a secondary display zone. The secondary display zone has a plurality of sensors. The display device decides the number of the sensors to enable according to the concentration-related signal.

In one embodiment, the display device further includes a secondary display zone. The secondary display zone has a plurality of light units. The display device decides the number of the light units taken to light according to the concentration-related signal. The higher the concentration of the user is, the more the number of the light units taken to light is.

A display device according to the invention includes a body having a display surface. The display surface includes a display zone for hour and a display zone for minute. The display zone for hour is located at the center region of the display surface and display an hour information. The display zone for minute surrounds the display zone for hour and display a minute information.

In one embodiment, the display zone for hour and the display zone for minute do not overlap.

In one embodiment, the display zone for hour and the display zone for minute have a plurality of light units allocated thereat to display the hour information and the minute information.

In one embodiment, the light units are sequentially taken to light and thus to form the hour information.

In one embodiment, the light units are disposed at the display zone for minute and sequentially taken to light and thus to form the minute information.

In one embodiment, the display surface is located at a first surface of the body. The display zone for hour is located at the center region of the display surface. The display zone for minute is located at the peripheral of the body.

In one embodiment, the body further includes a display zone for second to display a second information.

In one embodiment, the display zone for second is allocated at the lateral wall of edge of the display device. The display zone for second has a plurality of light units disposed thereon. The light units are sequentially taken to light and thus to emit light toward the edge of the body to display the second information.

In one embodiment, the display zone for second is allocated at a secondary surface of the display device. The secondary surface and the first surface are opposite to each other. The display zone for second has a plurality of light units disposed thereon. The light units are sequentially taken to light and thus to emit light toward the edge of the display device to display the second information.

In one embodiment, the display device further includes a switch disposed on the body. The display device display the hour information and the minute information after the switch is conducted.

In summary, as to the interactive system and its display device and brainwave detection device, the brainwave detection device detects the brainwave information of a user and issues a concentration-related signal according to the brainwave information. The display device has a first display zone which can display a plurality of patterns. By receiving the concentration-related signal, the content of the concentration-related signal can be utilized to decide the display duration of the patterns. Therefore, the user can decide the display duration of the patterns according to his concentration level, so the interactive system can act as a game system which interacts with the brainwave information of the user.

In addition, the invention also provides a display device which can act as a clock. The display surface is divided into a display zone for hour and a display zone for minute respectively to display an hour information and a minute information. By way of this configuration, the invention provides a clock which is compact and easy to read time information.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

The embodiments of the invention will be apparent from the following detailed description, which proceeds with reference to the accompanying drawings, wherein the same references relate to the same elements.

Figure 1:
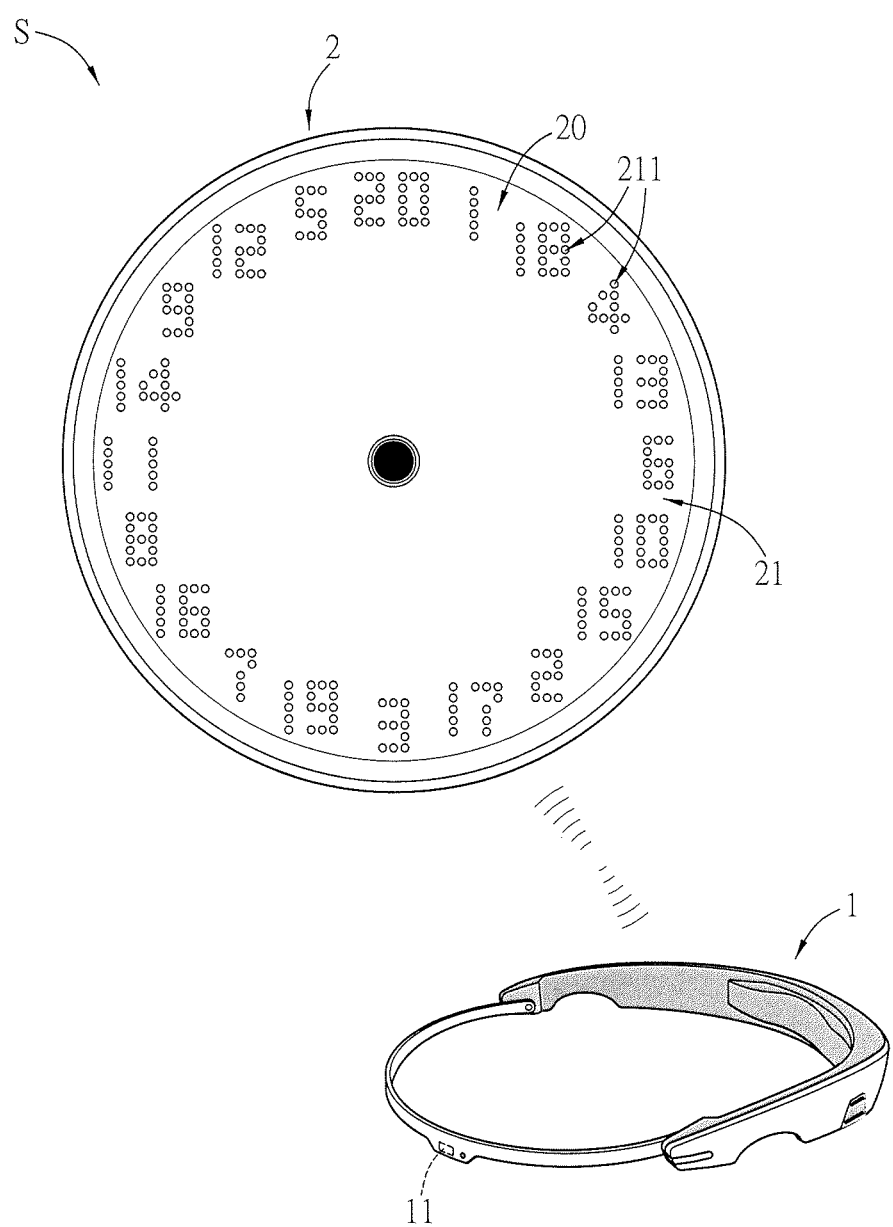
FIG. 1 is a schematic view showing an interactive system according to the embodiment of the invention.

FIG. 1 is a schematic view showing an interactive system according to the embodiment of the invention. Referring to FIG. 1, the interactive system S includes a brainwave detection device 1 and a display device 2. The display device 2 receives the signal from the brainwave detection device 1 to interact with each other.

Figure 2:
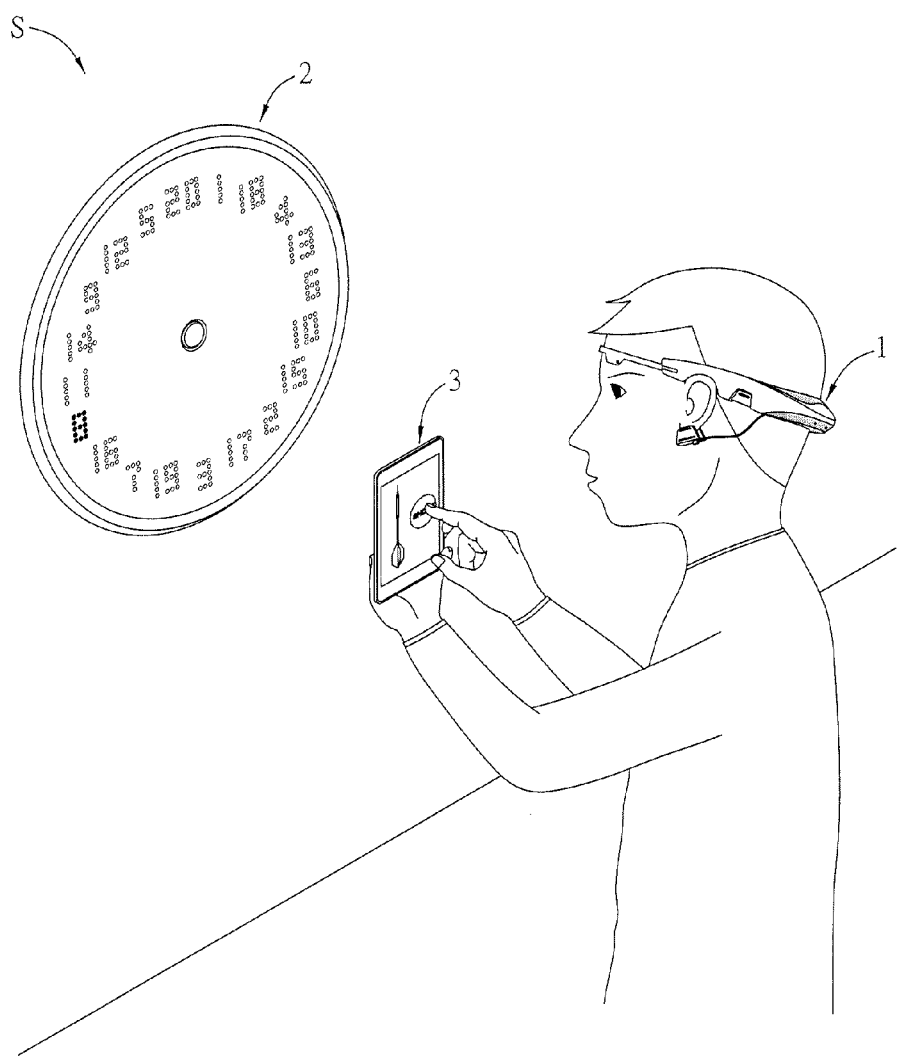
FIG. 2 is a schematic view showing that the interactive system in FIG. 1 cooperates with an electronic device.

FIG. 2 is a schematic view showing that the interactive system in FIG. 1 cooperates with an electronic device. Referring to FIG. 1 and FIG. 2, the interactive system S in the embodiment cooperates with an electronic device 3. Each unit of the interactive system S and the electronic device 3 can transmit signals to each other. The type of the electronic device 3 is not limited. It refers to a device capable of fundamental computing, preferably a hand-held, portable or gripped electronic device 3. For example, it may be a mobile phone or a tablet computer, or a watch, or a band, or a wearable electronic device with small volume and easy to wear such as a ring, etc. In the embodiment, the electronic device 3 is a smart phone for example. Practically, the user interacts with the interactive system S through the electronic device 3. Preferably, the interactive system S cooperating with the electronic device 3 may be applied to an interactive game system.

Referring to FIG. 1, the brainwave detection device 1 includes a detection electrode 11. The location of the detection electrode 11 is not limited in the invention, so it may be located at any place of the brainwave detection device 1. Preferably, it may be located disposed on one side which is at the face of the user during wearing like this embodiment. The detection electrode 11 detects the brainwave information of a user, preferably the brainwave information of the user wearing the detection electrode 11. After receiving the brainwave information, the detection electrode 11 can issue a concentration-related signal according to the brainwave information. As to the concentration-related signal, because the user has different concentrations at different times, the brainwave information (namely brain wave) correspondingly generated have different frequencies and waveforms. The detection electrode 11 can thus transform the brainwave information generated at different concentration levels correspondingly into different concentration-related signals so as to execute a follow-up application by the interactive system in the embodiment.

In the embodiment, the display device 2 is a disk-like object, but it is not limited to. The display device 2 may also be in any shape such as rectangular shape, or elliptical, etc. The display device 2 includes a display surface 20. The display surface 20 has a first display zone 21. The first display zone 21 display a plurality of patterns 211. The first display zone 21 is not limited to its distributive regions. The first display zone 21 in the embodiment is defined by the regions which the patterns 211 are distributed over and cover. The distributed locations of the patterns 211 on the display surface 20 is not limited in the invention.

Figure 3:
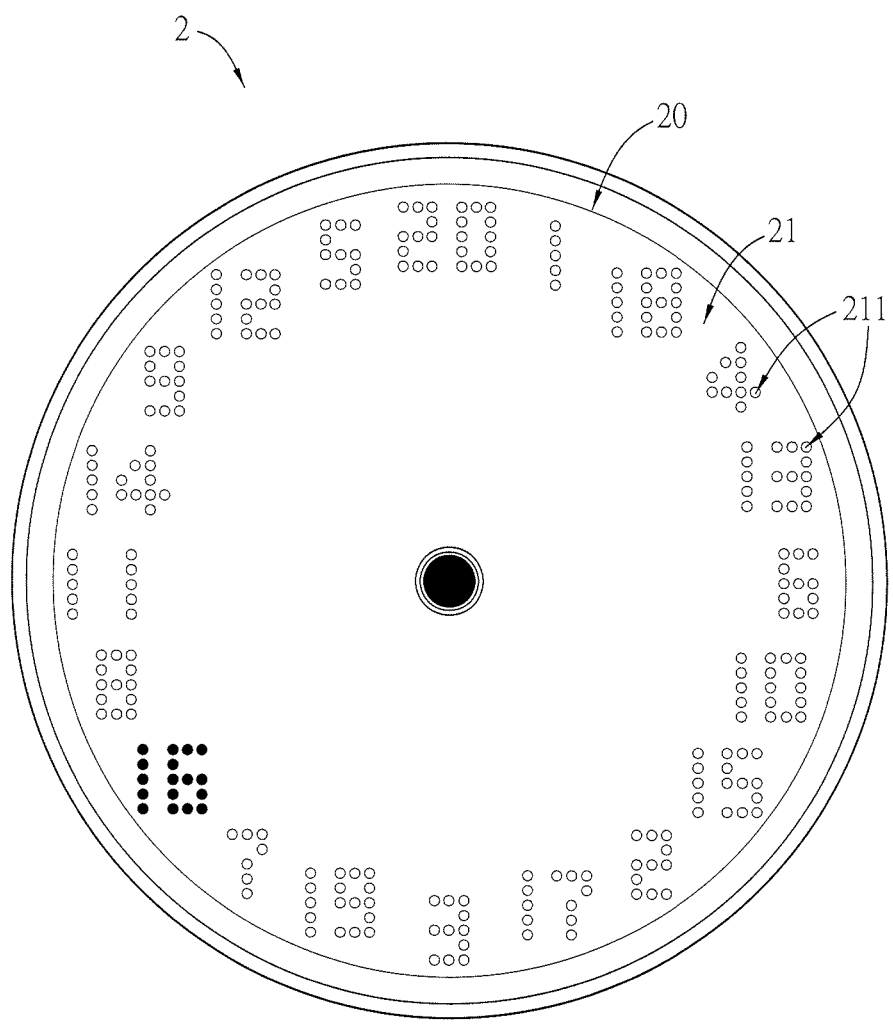
FIG. 3 is a schematic view showing the display device of the interactive system in FIG. 1 at different states.

Then, the detail of the first display zone 21 is explained. FIG. 3 is a schematic view showing the display device of the interactive system in FIG. 1 at different states. Referring to FIG. 1 and FIG. 3, in the embodiment, the patterns 211 are distinct numerals but they are not limited to. The patterns 211 may be the numerals which are at least partly the same, and they are not limited to numerals in practice. For example, the patterns 211 may be different designs.

The patterns 211 may be formed by a plurality of pixels or LEDs (light-emitting diode) to light and display the content of the patterns 211. The first display zone 21 may be implemented by a flat display so that the first display zone 21 can have a plurality of pixels. In these embodiments, the flat display may be an LCD (liquid crystal display), an OLED (organic light-emitting diode) display, or an electronic paper, and it is not limited to. Besides, the patterns 211 may be displayed clockwise, counterclockwise or randomly in turn on the first display zone 21, or alternatively the multiple patterns 211 are displayed at the same time, and they are not limited to.

As mentioned above, because the interactive system S in the embodiment is applied to an interactive game system for example, the user can play the game by operating the electronic device 3. For example, the electronic device 3 acts as a controller or a remote controller, and the display device 2 acts as an electronic display panel. When the display device 2 displays at least one of the patterns 211 at a specific time, the user can operate the electronic device 3 to correspondingly obtain the interactive result involved in the patterns 211. Because the actual operation method of the interactive system S in the embodiment will be explained later, it is not repeated here.

Figure 4A:
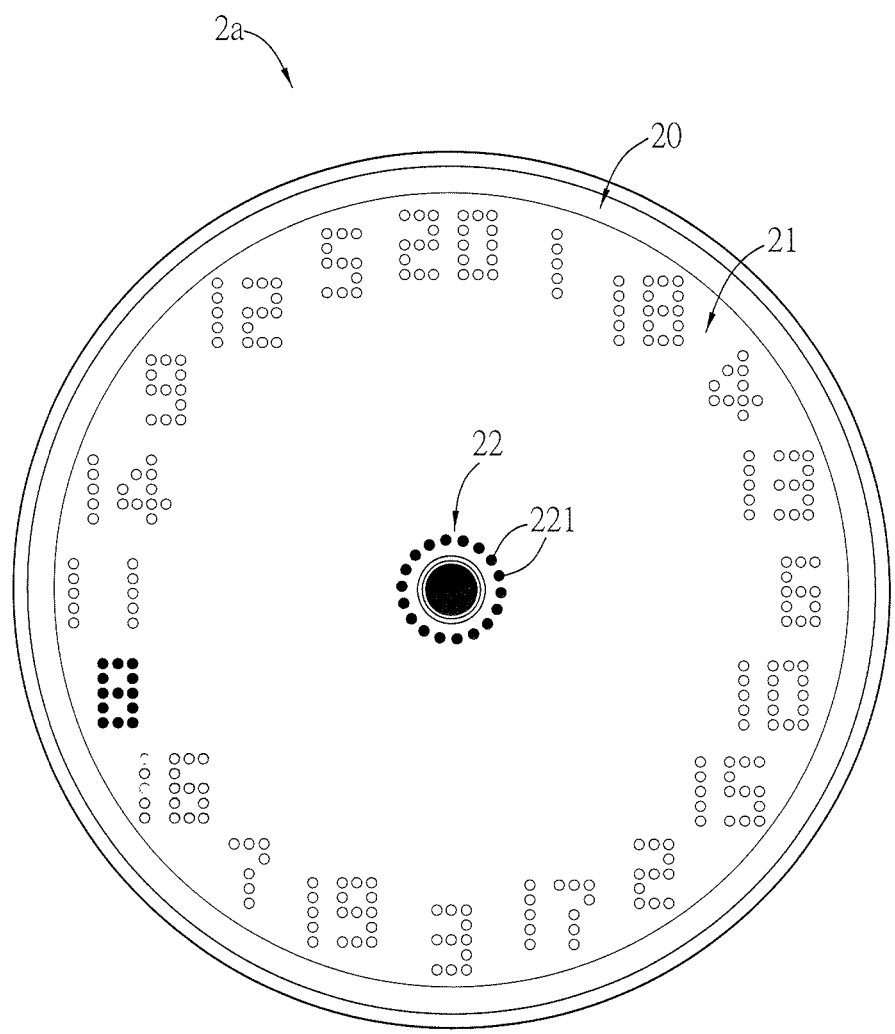
FIG. 4A and FIG. 4B are schematic views showing the exterior of the display device according to another embodiment of the invention.
Figure 4B:
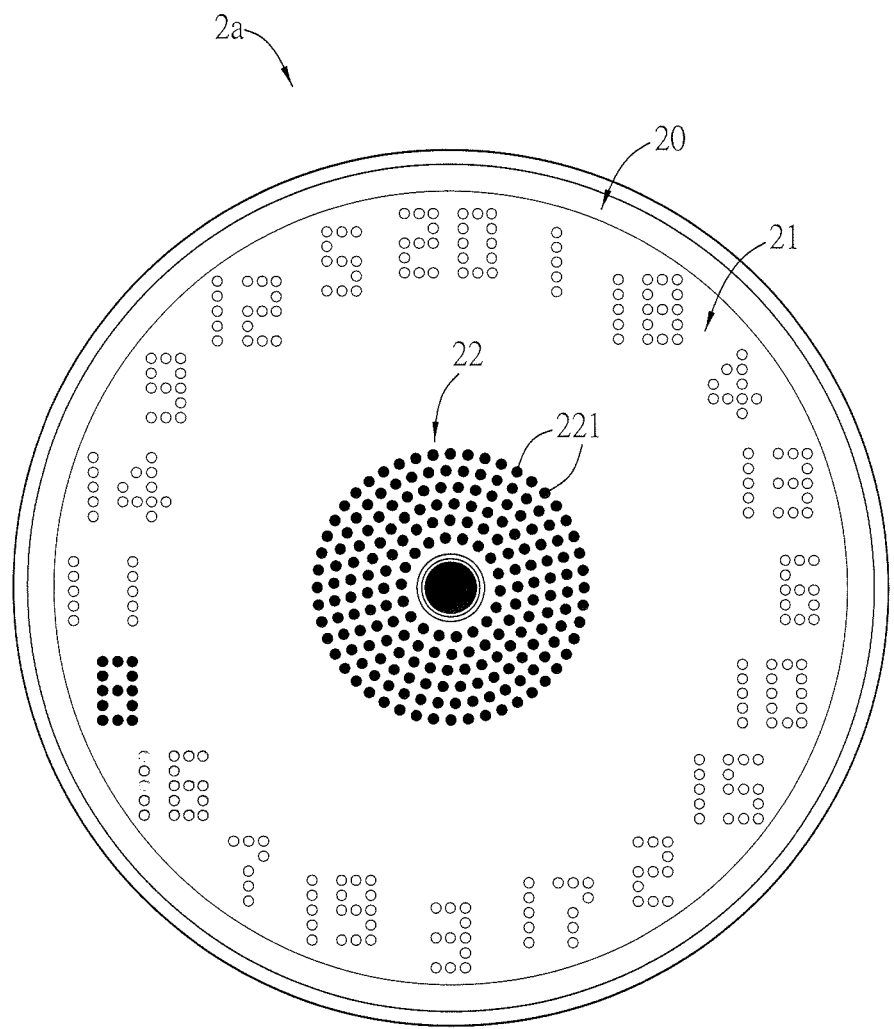

Referring to FIG. 4A and FIG. 4B, FIG. 4A and FIG. 4B are schematic view showing the exterior of the display device according to another embodiment of the invention. The display device 2a shown in FIG. 4A and FIG. 4B includes a secondary display zone 22 in addition to the first display zone 21. The first display zone 21 and the secondary display zone 22 are located at the display surface 20 of the display device 2a together and they do not overlap. In the embodiment, the first display zone 21 surrounds the secondary display zone 22, but they are not limited to. In other embodiments, the locations of the first display zone 21 and the secondary display zone 22 may be exchanged or arranged in other manners.

In the embodiment, the secondary display zone 22 has a plurality of light units 221. The light units 221 include at least one pixel or at least one LED. The display device 2a will decide the number of the light units 221 taken to light according to the concentration-related signal. Because the light number and light mechanism of each light unit 221 of the secondary display zone 22 will be explained with the later embodiment of the interactive system, they are not repeated here.

To clarify the details of the elements of the interactive system and their actual functions, the method of operating the interactive system and the components cooperating with the interactive system will be apparent from the following detailed description. However, it is noted that the contents of the below embodiments are illustrated for example but not limited. In addition to the display device 2a, the brainwave detection device applied in the embodiment is similar to or the same with the brainwave detection device 1 of the interactive system S, so the detail can refer to FIG. 1.

Here, it is noted that the electronic device 3 has an application program built in by software or firmware in advance. By this application program, the user can execute different operations on the electronic device 3.

Figure 5A:
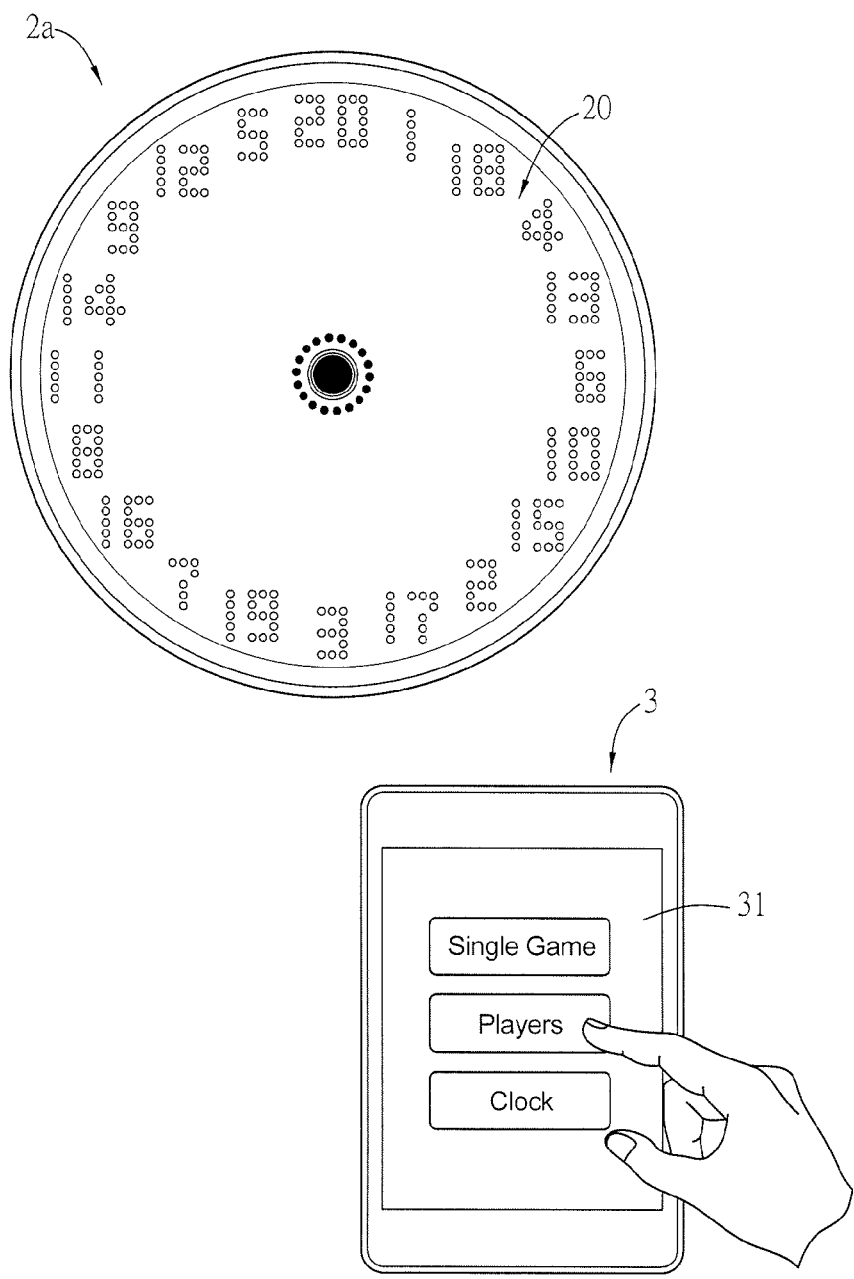
FIGS. 5A-5E are schematic views showing a series of operations of the operation method of the interactive system by utilizing the display device in FIG. 4A.
Figure 5B:
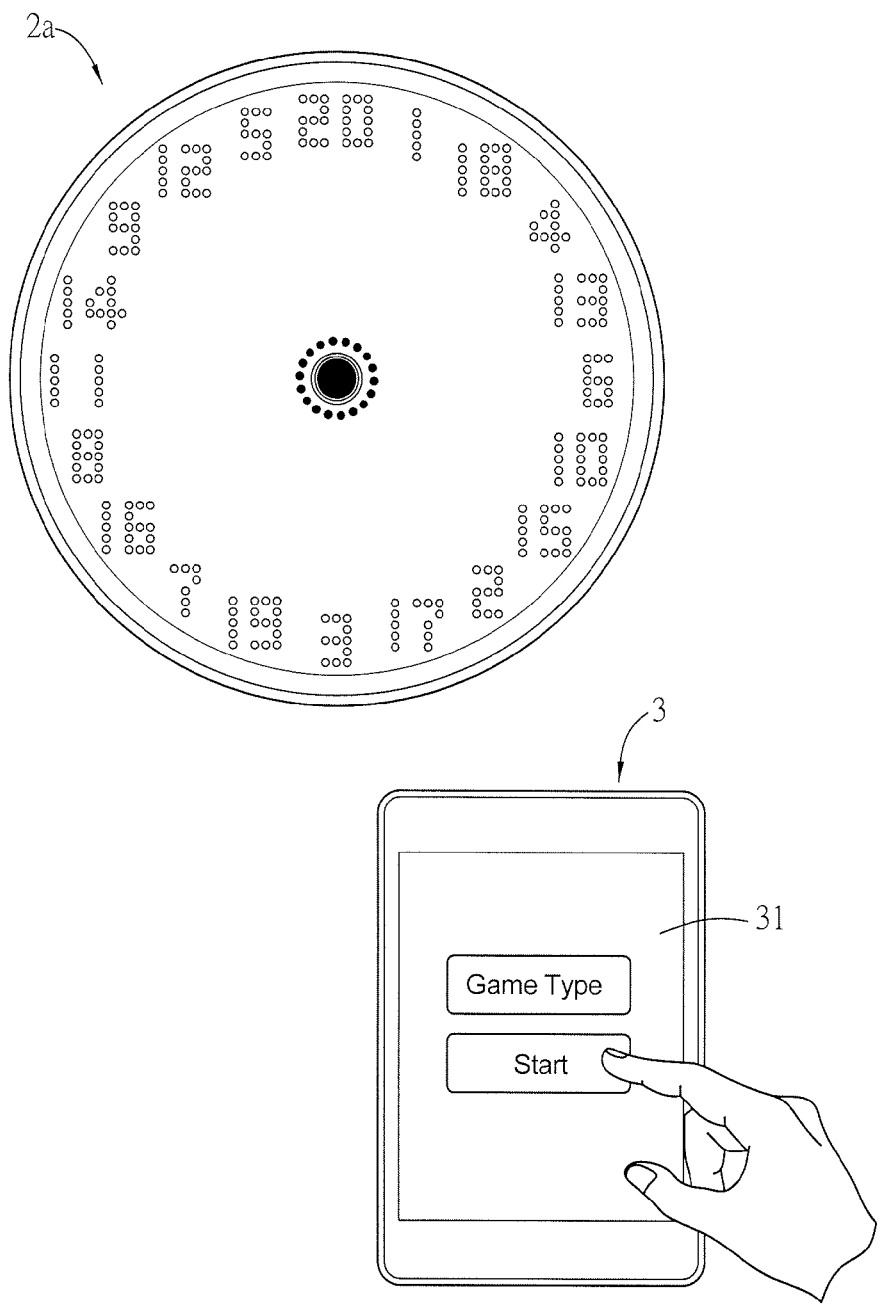

FIGS. 5A-5E are schematic views showing a series of operations of the operation method of the interactive system by utilizing the display device in FIG. 4A Referring to FIG. 5A to FIG. 5E, first, an application program is started on the electronic device 3, and a menu for operation is display on the operation interface. The menu is provide for the user to select a mode, for example, single player mode, multiplayer mode, or clock mode (as shown in FIG. 5A), and to select the item to choose the game mode or to select the item to start the game (namely start the interactive system)(as shown in FIG. 5B).

Here, it is noted that the display device 2a in the embodiment may also display time by the display surface 20 to act as a clock. Because the detail of clock mode will be explained later, it is not repeated here.

Figure 5C:
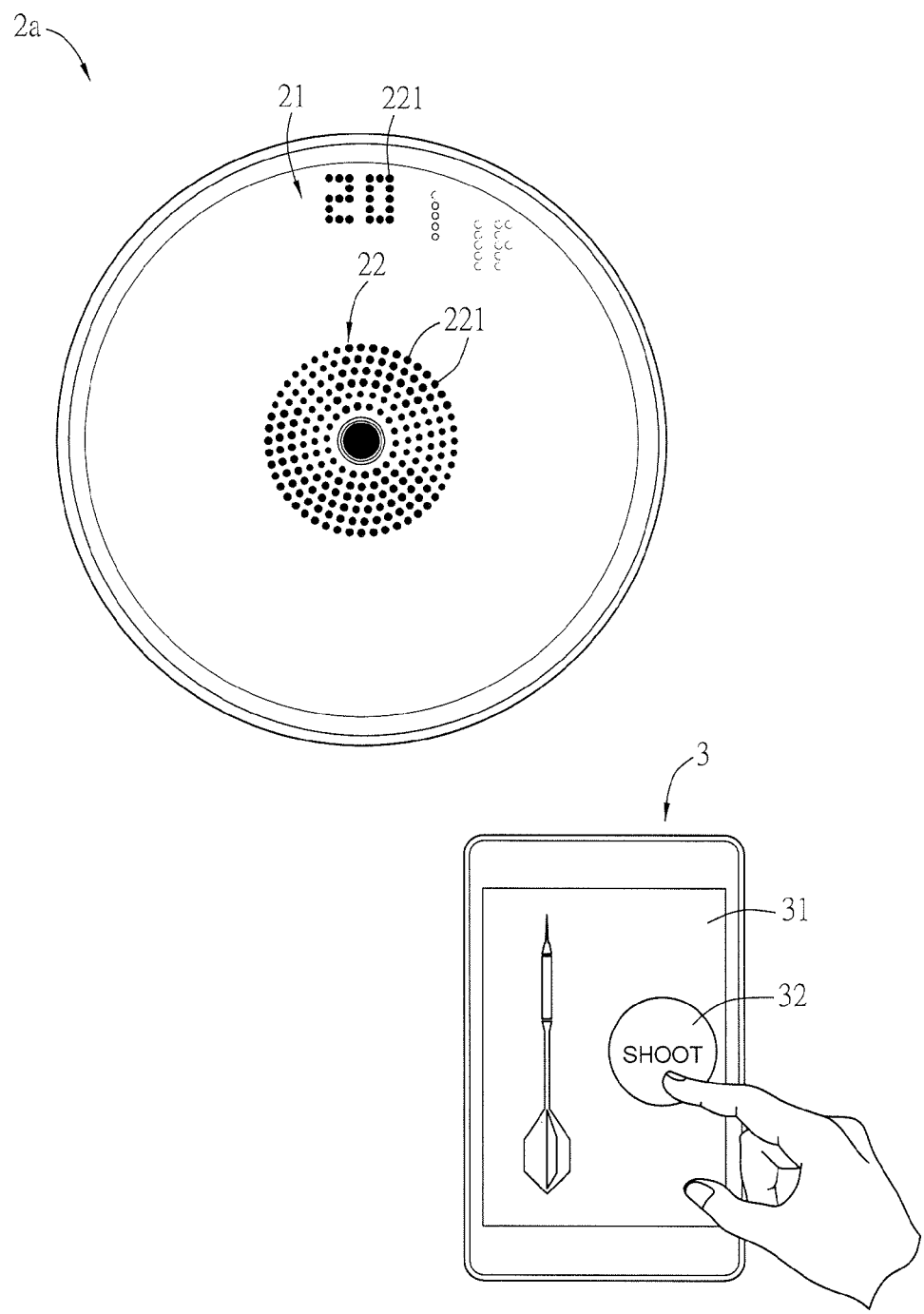
Figure 5D:
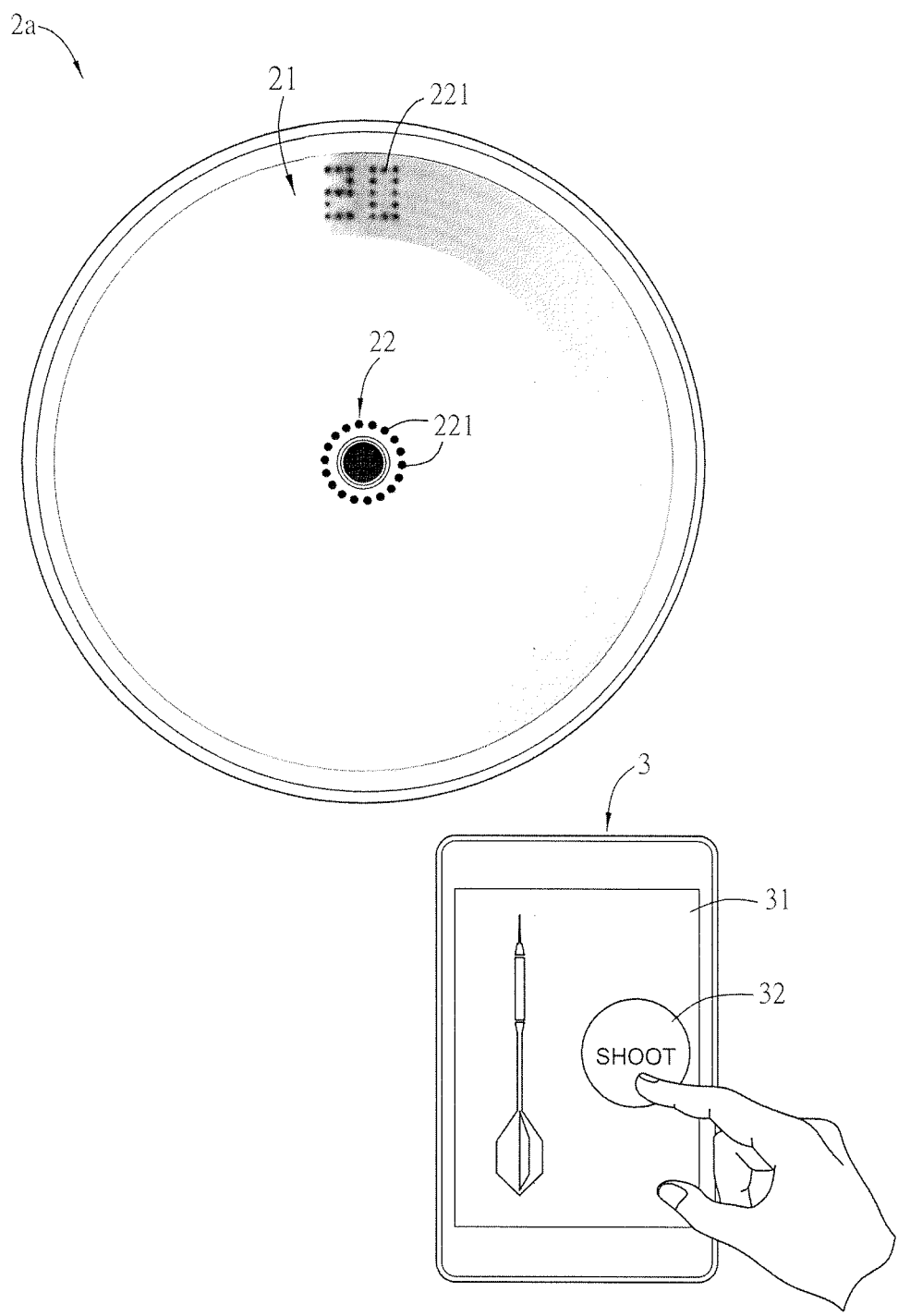
Figure 5E:
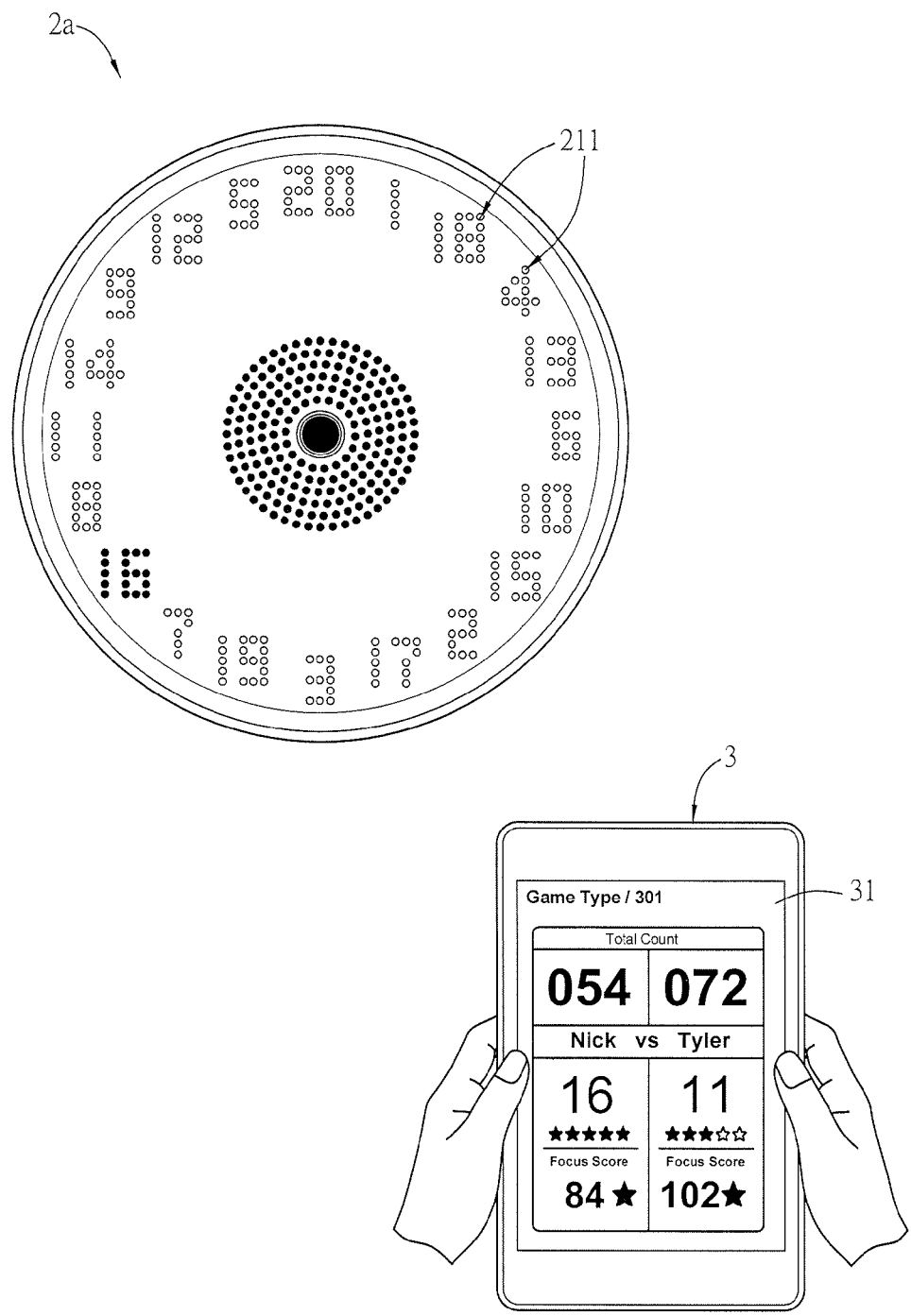

Referring to FIG. 1, FIG. 5C and FIG. 5D, when the interactive system starts to execute, the brainwave detection device 1 detects the brainwave information of the user and issues a concentration-related signal according to the detected brainwave information. The brainwave detection device 1 performs the detection continuously or at a predetermined time interval. In the embodiment, the display 2a receives the concentration-related signal issued from the brainwave detection device 1 through the electronic device 3. The electronic device 3 sends the concentration-related signal to the display device 2a. However, they are not limited thereto. Practically, the display device 2a may directly receive the concentration-related signal issued from the brainwave detection device 1.

Then, the display device 2a decides the display duration of at least one of the patterns according to the concentration-related signal. In detail, the higher the concentration of the user is which is represented by the concentration-related signal received by the display device 2a, the more the display time of the patterns 211 is. In other words, each pattern 211 displays for a longer period of time, and thus the content displayed by the patterns 211 are easier for the user to watch.

As mentioned above, at the moment of detecting brainwave, the user can watch the pattern displayed by the display device 2a. When the pattern 211 (for example score) displayed by the display device 2a is the pattern which the user prefers to select (for example the score is higher), the user can perform a default operation by the default zone of the operation interface of the electronic device 3. The default zone for example is the location of the item 32 ("SHOOT") shown in FIG. 5C. When the user presses (or touches) it, the electronic device 3 accordingly issues an executing signal to the display device 2a. After receiving the executing signal, the display device 2a display a first interactive result and/or a secondary interactive result according to the executing signal.

In detail, the first interactive result is that the patterns 211 (the patterns 211 in the embodiment are a darts score) correspondingly displayed by the first display zone 21 when the display device 2a is receiving the executing signal. In other words, the first interactive result at this moment is the score. The secondary interactive result is that the state of the light units 221 correspondingly displayed by the secondary display zone 22 when the display device 2a is receiving the executing signal. The state of the light units 221 means the number of the light units 221 taken to light and the distributing area of the light units taken to light. In the embodiment, the higher the concentration of the user is, the more the number of the light units 221 taken to light is/or the more the distributing area of the light units 221 taken to light is (as shown in FIG. 5C). On the contrary, the lower the concentration of the user is, the less the number of the light units 221 taken to light is/or the less the distributing area of the light units 221 taken to light is (as shown in FIG. 5D). The light units 221 of the secondary display zone 22 in the embodiment are grouped into rings. During displaying, when the concentration of the user transits between high and low status, it is observable that the light units 221 are lighting or going off in multiple rings. However, the display mechanism of the secondary interactive result is not limited, and it depends on actual requirement of the user or the manufacturing process to adjust.

As mentioned above, when the concentration of the user is higher, what the display device 2a displays is shown in FIG. 5C, and it accordingly includes the first display zone 21 having the patterns 211 whose display time is longer and a secondary display zone 22 having the light units 221 being lighting of which the number is more. On the contrary, as shown in FIG. 5D, when the concentration of the user is lower, the display time of the patterns 211 of the first display zone 21 is relatively shorter (namely, two patterns 211 switch faster), and the number of the light units 221 being lighting at the secondary display zone 22 is relatively less.

By scoring the first interactive result and the secondary interactive result, the score accumulated by the patterns 211 and the concentration level scored by the secondary interactive result can be respectively obtained. After finishing the operation mode of the interactive system, the display interface 31 of the electronic device 3 can accordingly display the result shown in FIG. 5E.

Figure 6:
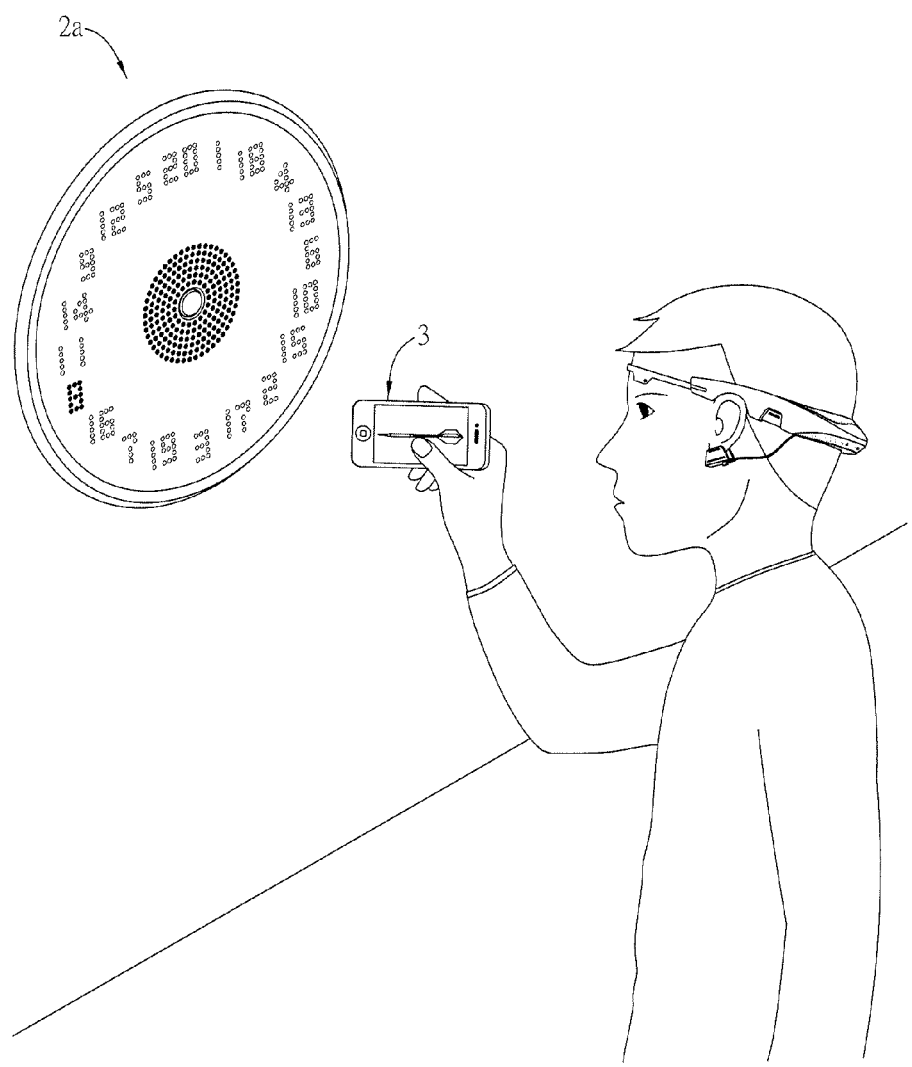
FIG. 6 is a schematic view showing that the interactive system by utilizing the display device in FIG. 4A cooperates with an electronic device.

However, the operation method of the interactive system cooperating with the electronic device according to the invention is not limited to the above mentioned method. In other embodiments, referring to FIG. 6, FIG. 6 is a schematic view showing that the interactive system in FIG. 4A cooperates with an electronic device. The user can sway the electronic device 3 to issue the executing signal. In other words, the default operation for the user to the electronic device 3 can be defined as swaying the electronic device 3, and thus the user can interact by the action similar to throwing actual darts so as to be entertaining.

In the embodiment, in order to enhance the experiences of presence for the user during interacting, the secondary display zone 22 of the display device 2 has a plurality of sensors (not shown in figure). The display device decides the number of the sensors to enable according to the concentration-related signal. Although the location of the sensor is not limited, it is preferably disposed within the secondary display zone 22 (in the embodiment, it is closer to the center of the display device 2a with respect to the first display zone 21).

Besides, when the default operation is defined as swaying the electronic device 3, as to the number/the lighting area of the light units 221 of the secondary display zone 22 which are lighting with respect to the user, the higher the concentration of the user is, the more the number of the light units 221 of the secondary display zone 22 which are lighting/or the wider the lighting area of the light units 221 of the secondary display zone 22. It is beneficial for the user to aim the bullseye of the display device 2a and to throw accurately toward the sensors of the display device 2a.

The invention also provide a display device and a brainwave detection device. The display device cooperates with a brainwave detection device. The brainwave detection device cooperates with an electronic device and a display device. Because the formation, feature and implementation of the display device and the brainwave detection device mentioned here are approximately similar to or the same with the interactive system S and its cooperating electronic device 3 in the previous embodiments which have been explained above, they are not repeated here again.

Figure 7:
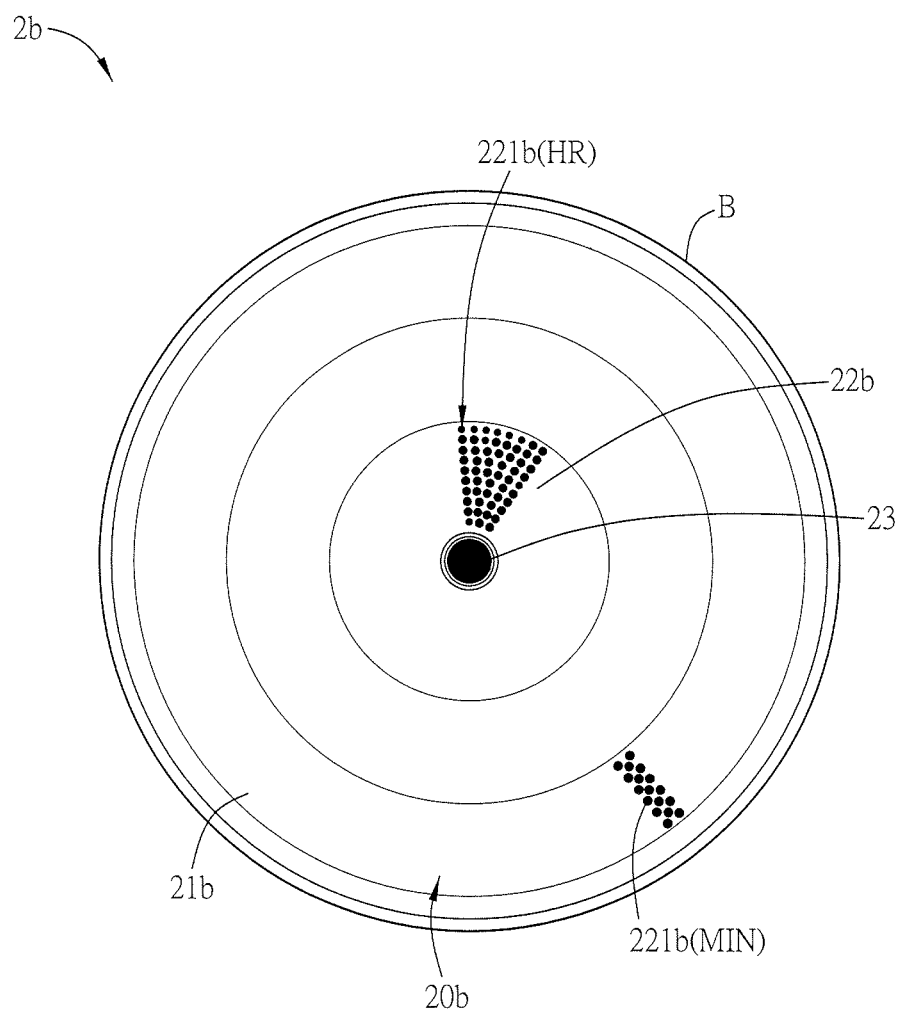
FIG. 7 is an external view showing that the display device according to one embodiment of the invention is applied to a clock at a first mode.

A display device 2b is also provided to apply to a clock. Referring to FIG. 7, it is an external view showing that the display device according to one embodiment of the invention is applied to a clock at a first mode. The detail of the display device 2b is approximately similar to or the same with those of the display devices 2, 2a, and thus only the structure feature of the display device 2b applied to the clock is explained below.

The display device 2b in the embodiment includes a body B. The body B has a display surface 20b. In the embodiment, the display surface 20b is allocated at the first surface S1 of the body B. The surface opposite to the first surface S1 is the secondary surface S2 (not labelled in the figure but can refer to FIG. 10). It is noted that the explanation here is for easily understanding the technique feature but not limited thereto.

The display surface 20b of the display device 2b includes a display zone for minute 21b and a display zone for hour 22b (namely the first display zone and the secondary display zone in the previous embodiments). Further, the display zone for hour 22b is located at the center region of the display surface 20b. The display zone for minute 21b surrounds the display zone for hour 22b. In other words, the display zone for minute 21b is located at the peripheral of the body B. The display zone for hour 22b and the display zone for minute 21b do not overlap. It is noted that the locations of the display zone for hour 22b and the display zone for minute 21b in the embodiment are not limited. In other embodiments, the locations of the display zone for minute 21b and the display zone for hour 22b may exchange to achieve similar results.

The display zone for hour 22b displays an hour information HR. The display zone for minute 21b displays a minute information MIN. For example, when the time is 12:25, the display zone for hour 22b displays an hour hand between twelve o'clock and one o'clock as the hour information HR, and the display zone for minute 21b displays a minute hand toward five o'clock as the minute information MIN. In the embodiment, the manner of labeling time information is the same with that of traditional hands, but it is not limited thereto. In an alternatively embodiment, it may be displayed by numerals. For example, when the time is 12:25, the display zone for hour 22b displays numeral "12" toward twelve o'clock, and the display zone for minute 21b displays numeral "25" toward five o'clock.

Referring to FIG. 7, the display zone for minute 21b has a plurality of light units 211b to display the minute information MIN. Similarly, the display zone for hour 22b also has a plurality of light units 221b to display the hour information HR. Practically, the light units 211b, 221b are sequentially taken to light and thus to form the hour information HR and the minute information MIN. For example in FIG. 7, in order to display the time 12:25 by the clock 1, at least one part of the light units 221b between twelve o'clock and one o'clock in the display zone for hour 22b are taken to light, and at least one part of the light units 211b toward five o'clock in the display zone for minute 21b are taken to light. Then, when the time is 12:26, the light units 211b which are taken to light originally are extinguished instead, and part of the light units 221b adjacent to the light units 211b, which are originally taken to light, are taken to light instead, and so on. Therefore, the user can know the current time according to the pixels taken to light.

Besides, the display device 2b in the embodiment includes a switch 23b. The switch 23b can be disposed on the center, the peripheral or the secondary surface S2 of the body B. In the embodiment it is on the center for example but not limited to. The switch 23b for example can be a button or a knob. It decides whether to conduct the circuit of the display device 2b according to the status of pressing or turning, so as to enable the display device 2b to display the hour information and the minute information.

Figure 8:
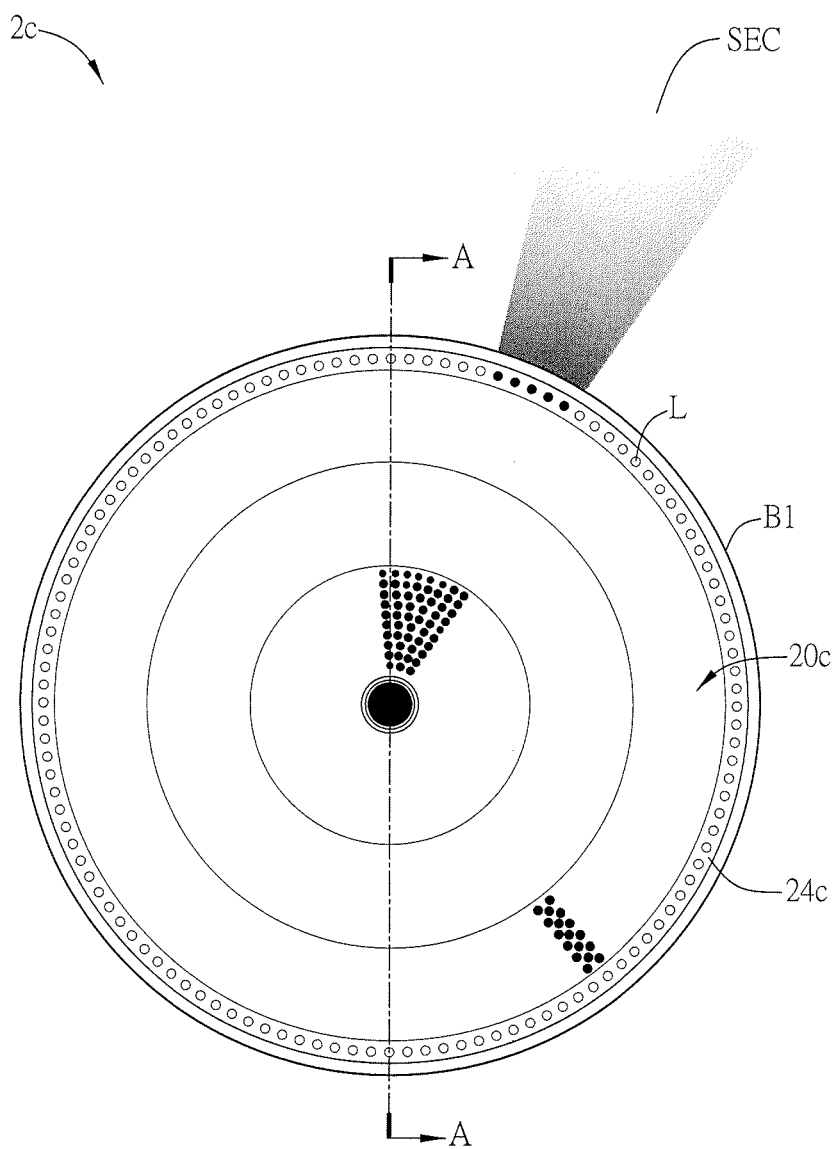
FIG. 8 is an external view showing that the display device according to another embodiment of the invention is applied to a clock at the first mode.
Figure 9:
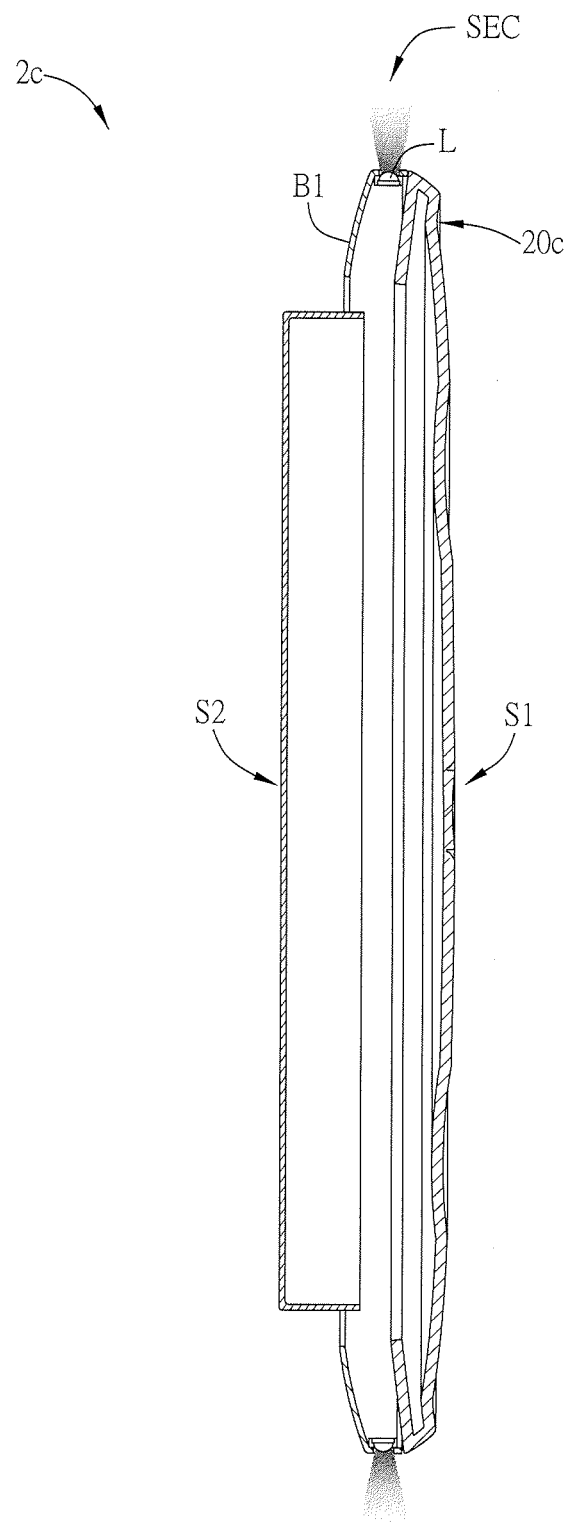
FIG. 9 is a sectional view showing a clock along line A-A in FIG. 8 according to one embodiment of the invention.

Then, referring to FIG. 8 to FIG. 9, FIG. 8 is an external view showing that the display device according to another embodiment of the invention is applied to a clock at the first mode, and FIG. 9 is a sectional view showing a clock along line A-A in FIG. 8 according to one embodiment of the invention.

The display device 2c in the embodiment similarly includes a body B1. The body B1 also has a display surface 20c to display the hour information HR and the minute information MIN. The difference from the previous embodiments is that the body B1 in the embodiment further includes a display zone for second 24c to display a second information SEC. The display zone for second 24c is allocated at the lateral wall of edge of the body B1. The display zone for second 24c has a plurality of light units L disposed thereon. The light units L are sequentially taken to light and thus to emit light toward the edge of the body B1 to display the second information SEC. The light units L are taken to light at a period of 60 seconds (cooperating with the second information). The light units L may respectively be an LED.

The display zone for second is allocated at the secondary surface of the body. The secondary surface and the first surface are opposite to each other. The display zone for second has a plurality of light units disposed thereon. The light units are sequentially taken to light and thus to emit light toward the edge of the body to display the second information.

FIG. 9 is a sectional view showing a clock along line A-A in FIG. 8 according to one embodiment of the invention. Referring to FIG. 8 and FIG. 9, in the embodiment, the light units L are allocated at the peripheral of the body B1. When the light units L are sequentially taken to light, the light is emitted toward the edge of the display device 2c. Thus the emitted light beam can be seen by the user to form the second information SEC.

Figure 10:
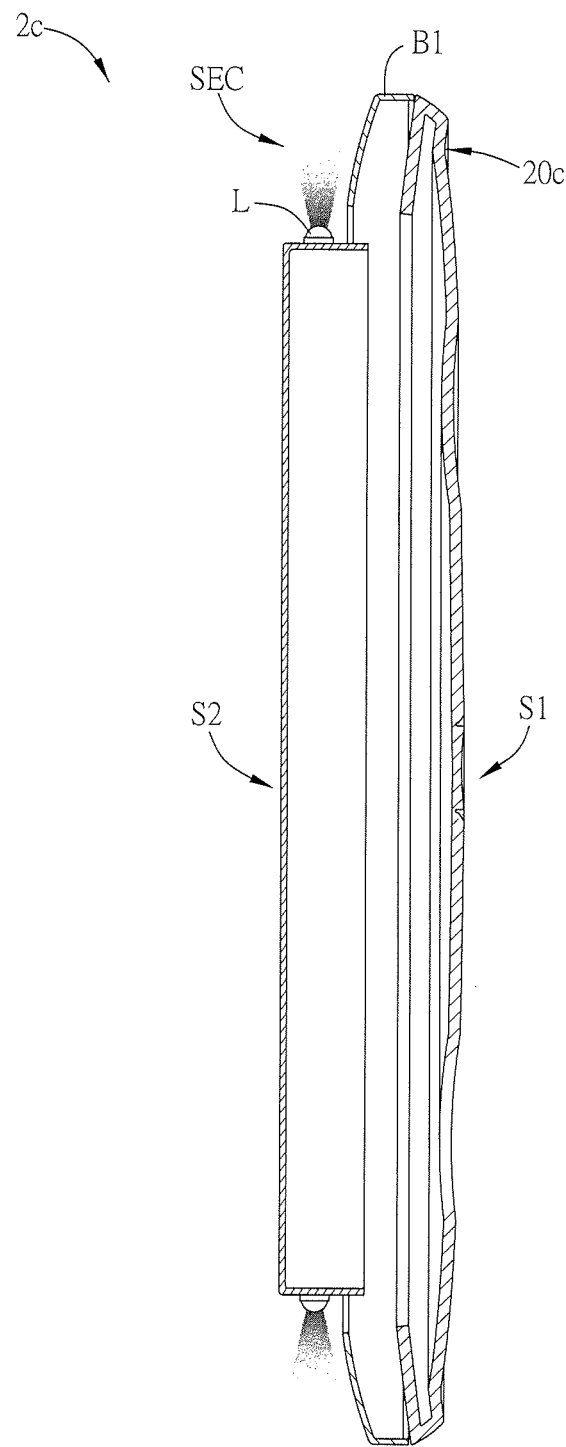
FIG. 10 is a sectional view showing a display device along line A-A in FIG. 8 according to another embodiment of the invention.

Finally, referring to FIG. 10, FIG. 10 is a sectional view showing a display device along line A-A in FIG. 8 according to another embodiment of the invention. Referring to FIG. 8 and FIG. 10, in other embodiments, the light units L can be allocated on the secondary surface S2 of the body B1, and the secondary surface S2 and the first surface S1 are opposite to each other. The light units L allocated at the display zone for second 24c are sequentially taken to light and thus to emit light toward the edge of the body B1 to form the second information SEC like the clock in FIG. 9. In the embodiment, because the light units L are allocated on the secondary surface S2 of the body B1, the thickness of the edge of the body B1 is not increased if the light units L are allocated in the embodiment.

In summary, as to the interactive system and its display device and brainwave detection device, the brainwave detection device detects the brainwave information of a user and issues a concentration-related signal according to the brainwave information. The display device has a first display zone which can display a plurality of patterns. By receiving the concentration-related signal, the content of the concentration-related signal can be utilized to decide the display duration of the patterns. Therefore, the user can decide the display duration of the patterns according to his concentration level, so the interactive system can act as a game system which interacts with the brainwave information of the user.

In addition, the invention also provides a display device which can act as a clock. The display surface is divided into a display zone for hour and a display zone for minute respectively to display an hour information and a minute information. By way of this configuration, the invention provides a clock which is compact and easy to read time information.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A clock, adapted to operate in a first mode and a secondary mode, comprising:
   a body, having a display surface,
     wherein when the clock operates in the first mode, the clock displays a time information on the display surface,
     wherein when the clock operates in the secondary mode, the clock acts as a dart board and receives at least one external signal, and the clock displays at least one interactive information on the display surface according to the external signal,
     wherein the display surface is allocated on a first surface of the body, the body further comprises a plurality of light units disposed on a peripheral surface of the body or a peripheral surface extending from a secondary surface of the body towards the first surface, the secondary surface of the body is opposite to the first surface, wherein in the first mode, the light units are sequentially taken to light so as to emit light toward the edge of the body to display seconds information.

2. The clock of claim 1, wherein in the first mode, the display surface has a first display zone and a secondary display zone, the first display zone surrounds the secondary display zone, the first display zone displays a minute information, and the secondary display zone displays an hour information.

3. The clock of claim 1, wherein the first display zone and the secondary display zone respectively have a plurality of light units to respectively display the minute information and the hour information.

4. The clock of claim 3, wherein in the first mode, the first display zone and the secondary display zone do not overlap.

5. The clock of claim 1, wherein in the secondary mode, the external signal is an executing signal, and the clock displays a pattern as the interactive information according to the executing signal.

6. The clock of claim 1, wherein in the secondary mode, the external signal is a concentration-related signal, the display surface comprises a third display zone, the third display zone displays a plurality of patterns, and the clock decides the display duration of at least one of the patterns according to the concentration-related signal.

7. The clock of claim 6, wherein the patterns comprises a dart board score information.

8. The clock of claim 6, wherein the patterns comprises a numeral or a design, and the patterns are displayed clockwise, counterclockwise or randomly in turn.

9. The clock of claim 1, wherein in the secondary mode, the external signal is a concentration-related signal, the display surface comprises a fourth display zone, the fourth display zone has a plurality of light units, and the clock decides the number of the light units taken to light according to the concentration-related signal, and the number of the light units taken to light is proportional to a concentration level of a user.

10. The clock of claim 1, further comprising:
    a switch, disposed on the body, wherein the clock is decided to operate in the first mode or the secondary mode according to the conduct status of the switch.

11. A clock, comprising:
    a body, having a display surface located at a first surface of the body and a display zone for seconds to display seconds information,
      wherein the display surface comprises:
        a display zone for hour, located at the center region of the display surface and displaying an hour information; and
        a display zone for minute, surrounding the display zone for hour and displaying a minute information,
      wherein the display zone for seconds is allocated at a lateral wall of an edge of the body or a peripheral surface extending from a secondary surface of the body toward the first surface, and the secondary surface and the first surface are opposite to each other,
      wherein the display zone for seconds has a plurality of light units disposed thereon, and the tight units are sequentially taken to light so as to emit light toward the edge of the body to display the seconds information.

12. The clock of claim 11, wherein the display zone for hour and the display zone for minute do not overlap.

13. The clock of claim 11, wherein the display zone for hour and the display zone for minute have a plurality of pixels allocated thereat to display the hour information and the minute information.

14. The clock of claim 13, wherein the pixels at the display zone for hour are sequentially taken to light and thus to form the hour information.

15. The clock of claim 13, wherein the pixels at the display zone for minute are sequentially taken to light and thus to form the minute information.

* * * * *